(12) United States Patent
Iwata et al.

(10) Patent No.: US 7,394,544 B2
(45) Date of Patent: Jul. 1, 2008

(54) ELUTION TEST METHOD AND APPARATUS

(75) Inventors: Yosuke Iwata, Kyoto (JP); Motoaki Mori, Tokyo (JP); Naoki Asakawa, Tokyo (JP)

(73) Assignees: Shimadzu Corporation, Kyoto-shi (JP); Eisai R&D Management Co., Ltd., Tokyo (JP)

( * ) Notice: Subject to any disclaimer, the term of this patent is extended or adjusted under 35 U.S.C. 154(b) by 284 days.

(21) Appl. No.: 11/389,714

(22) Filed: Mar. 27, 2006

(65) Prior Publication Data

US 2006/0213838 A1 Sep. 28, 2006

(30) Foreign Application Priority Data

Mar. 28, 2005 (JP) ............................. 2005-090700

(51) Int. Cl.
*G01N 21/00* (2006.01)
(52) U.S. Cl. ........................................ 356/432; 356/436
(58) Field of Classification Search ....................... None
See application file for complete search history.

(56) References Cited

U.S. PATENT DOCUMENTS 6,542,231 B1 *  4/2003  Garrett ........................ 356/246
2006/0204984 A1 *  9/2006  Bazan et al. .................... 435/6

* cited by examiner

*Primary Examiner*—Michael P. Stafira
(74) *Attorney, Agent, or Firm*—Rankin, Hill & Clark LLP

(57) ABSTRACT

An elution test method measures the elution process of a specific component in a process where a preparation containing at least the specific component subject to a change with time in chemical properties after elution and an impurity component not subject to a change with time in chemical properties after elution is eluted into a test liquid. The method obtains a ratio of absorbance k of the impurity component and a ratio of absorbance k' of the specific component at two isosbestic point wavelengths $\lambda 1$, $\lambda 2$ in a spectrum including the specific component and its decomposed matter, and calculates at least one of the absorbances $A1(t)$, $A2(t)$ of said specific component by using $k \times C2(t) - C1(t) = k \times A2(t) - A1(t)$ and $A1(t)/A2(t) = k'$ from the absorbance $C1(t)$, $C2(t)$ at said two isosbestic point wavelengths $\lambda 1$, $\lambda 2$ measured at the plural time points t in the elution process of said preparation, and converts the result to an elution concentration.

5 Claims, 9 Drawing Sheets

ELUTION TEST METHOD AND APPARATUS

The present application claims foreign priority based on Japanese Patent Application No. 2005-090700, filed Mar. 28, 2005, the content of which is incorporated herein by reference.

BACKGROUND OF THE INVENTION

1. Technical Field

The present invention relates to an elution test for evaluating the elution properties of a specific component contained in a pharmaceutical preparation. More specifically, the present invention relates to an elution test method for measuring the volume of solution of a specific component from a preparation such as a tablet or a capsule in an elution test liquid in a state (environment) similar to the inside of a digestive tube in order to obtain the elution concentration of the specific component, and elution test apparatus used for the method.

2. Related Art

In general, a pharmaceutical preparation undergoes a change in the elution properties and efficacy when only the size of a tablet is changed although the shape of medicine is the same. Even in case the size is unchanged, a different coating on the surface of the medicine leads to a change in the elution properties and the efficacy. When placing on the market a pharmaceutical preparation containing a specific component, an elution test is required for evaluating the properties of elution of the specific component into an elution test liquid. In case the specific component is not eluted within a predetermined time, it is judged that the expected efficacy is not obtained. The elution test liquid refers to an elution test liquid being acid (around pH1), weak acid (around pH4), or neutral (around pH7). In particular, in the case of a preparation that requires an in vitro-in vivo correlation, it is recommended to use a neutral test liquid as per the FDA guideline.

In the development of a pharmaceutical preparation, various preparation prescriptions are studies to establish a preparation prescription having optimum elution properties of a specific component so that the specific component will deliver in vivo with an expected efficacy. Such being the background, an elution test in the development of a pharmaceutical preparation involves a large number of samples to be evaluated. The elution test is cumbersome and takes time in analysis. Thus, a speedup of elution test operation is an essential requirement in the development of a pharmaceutical preparation.

In general, an elution test method for a pharmaceutical is defined in the Japanese Pharmacopoeia. Although the Japanese Pharmacopoeia defines the operation procedure in its elution test method, it does not include details on a method for calculating the elution concentration of a pharmaceutical from the data obtained.

As methods for determining the volume of pharmaceutical generally include absorbance measurement method (UV method) and the liquid chromatography (HPLC method).

The absorbance measurement method fills a test liquid containing a specific component eluted from a preparation in a certain cell of glass or quartz, measures the absorbance of the test liquid at a predetermined wavelength with a spectrophotometer, and obtains the degree of elution based on the working curve. The liquid chromatography separates a specific component alone via the liquid chromatography technique from a test liquid containing the specific component eluted from a preparation and obtains the degree of elution from the absorbance of the specific component by using a spectrophotometer.

The absorbance measurement method is simple and accurate so that it is often employed in quality management tests for pharmaceuticals. Its merits include a short analysis time and a small running cost required in analysis. In case an impurity component other than the specific component is mixed in the preparation, it is difficult to selectively determine the specific component alone. The impurity component generally refers to a component that hinders determination of the volume of the specific component, such as an antoxidant (such as ascorbic acid) or antiseptic and milderproofing agents contained in the preparation as well as a pharmaceutical additive having absorption in the ultraviolet or visible area.

The liquid chromatography is capable of separating a plurality of components in a preparation and determining their volumes, with demerits including a long analysis time and a larger running cost. For a substance whose specific component tends to change, the specific component changes during analysis in the liquid chromatography method that requires a long analysis time, thus making it difficult to obtain a precise value.

Generally, an elution test of a pharmaceutical evaluates the elution process of a specific component A alone assuming that the specific component is A and does not need to evaluate a decompressed matter A' that changed from the specific component A. However, in an elution test, concerning the specific component A that suffers from change, as an example, the volumes of the specific component A and the decompressed matter A' that changed from the specific component A are determined to determine the total component volume A+A', or the specific component A is converted to a decompressed matter A' or their derivative A" for measurement (refer to document Vo. 412, published by Federation of Pharmaceutical Manufacturers' Associations of Japan, "management of hardly-soluble pharmaceutical and variation pharmaceutical for the quality reevaluation").

To determine the volume of a specific component A and the decomposed matter A' that changed from the specific component A and obtain the total component volume A+A', general approaches include a method of separating the specific component A present in an eluate and the decomposed matter A' respectively by way of the HPLC method and obtaining the sum of their volumes, or a method of separating the specific component A present in an eluate and the decomposed matter A' respectively by way of the HPLC method to determine only the volume of the specific component A and correcting the volume of change from the specific component A to the decomposed matter A' by way of the Nelson-Wagner method that is based on the primary decomposition reaction and obtaining the elution ratio.

FIG. 10 shows a measurement example of decomposed matter A' by way of the Nelson-Wagner method. This method calculates the volume of change from the specific component A to the decomposed matter A' from the reaction velocity and obtains an elution profile via simulation. Note that in this method the reaction of the specific component A changing into the decomposed matter A' must be halted immediately after sampling, which makes the operation cumbersome.

In determination of a specific component in an elution test liquid by way of the absorbance measurement method, in case the preparation contains an impurity component having absorption in the ultraviolet or visible area other than the specific component, it is difficult to selectively determine the specific component alone. Further, in case the specific component easily changes in the test liquid, a precise elution volume is not determined. In the determination of the specific component in an elution test liquid by using the liquid chromatography, the reaction of the specific component must be halted through pH adjustment immediately after the sampling, which adds to cumbersome operation.

SUMMARY OF THE INVENTION

The invention may enhance the selectivity of a specific component in a test liquid even in case a specific component has changed or an impurity component coexists in the test liquid in an elution test using the absorbance measurement method in order to speed up the quality test of pharmaceuticals.

One or more embodiments of the invention provide an elution test method for measuring an elution process of a specific component in a process where a preparation containing at least the specific component subject to a change with time in chemical properties after elution and an impurity component not subject to a change with time in chemical properties after elution is eluted into a test liquid, the method comprising:

obtaining a ratio of absorbance k of the impurity component and a ratio of absorbance k' of the specific component at two isosbestic point wavelengths $\lambda 1, \lambda 2$ in a system including the specific component and its decomposed matter;

measuring at each time the absorbance C1(t), C2(t) in the two isosbestic point wavelengths for the test liquid at plural time points t of the elution process of the preparation and calculating at least one of the absorbances A1(t), A2(t) of the specific component by using the following relations:

$$k \times C2(t) - C1(t) = k \times A2(t) - A1(t) \quad (1) \text{ and}$$

$$A1(t)/A2(t) = k' \quad (2); \text{ and}$$

converting the result to an elution concentration.

The "system including the specific component and its decomposed matter" is not limited to a system including the two components, the specific component and the decomposed matter but the system may include a component shows spectrum does not a change with time. This is because such a components has no influence on detecting isosbestic point wavelengths.

The "decomposed matter" according to the invention is used as a concept covering all compounds chemically converted, such as a derivative.

When the absorption spectrum of a specific component and its decomposed matter are measured with the ratio concentration of both components changed while maintaining the total concentration, an absorption curve often has an intersection crossed at a single point. The intersection is called the "isosbestic point". The isosbestic point corresponds to a wavelength equal in terms of the mol absorbance of a specific component and its decomposed matter. This invention takes advantage of the fact that the absorbance of an isosbestic point is constant irrespective of the composition.

The term "elution" means elution of a specific component A in the preparation C into a test liquid. The term "decomposition" refers to the change of a specific component eluted into a test liquid to a component A' having different chemical properties by way of a physical or chemical change. The "decomposed matter" in this invention is used as a concept covering all compounds chemically converted, such as a derivative.

An isosbestic point wavelength may be obtained based on a differential of an absorption spectrum as well as the absorption spectrum itself. An elution test liquid also contains an impurity component whose chemical properties do not a change with time and the shape of whose spectrum does not change. Time differentiation of the absorption spectrum can eliminate the influence of the impurity component. In this invention, a wavelength having absorbance and its differential value being equal in intensity is defined as an isosbestic point wavelength.

The time differential value used is not particularly limited but may be an nth-order differential value, for example a first-order differential value, a second-order differential value, or a third-order differential value.

One or more embodiments of the invention provides an elution test apparatus comprising: an elution tester for eluting a preparation to be measured into a test liquid; a detector for irradiating light onto an eluate from the elution tester ad measuring an absorbance at two isosbestic point wavelengths $\lambda 1, \lambda 2$ in a system including a specific component and its decomposed matter contained in the preparation to be measured; and an arithmetic operation part for calculating at least one of the absorbances A1(t), A2(t) of the specific component by using $k \times C2(t) - C1(t) = k \times A2(t) - A1(t)$ and $A1(t)/A2(t) = k'$ from the absorbance C1(t), C2(t) at the two isosbestic point wavelengths $\lambda 1, \lambda 2$ measured at the plural time points t in the elution process of the preparation and converting the result to an elution concentration.

In the above relations, k represents the ratio of absorbance of the impurity component at the two isosbestic point wavelengths $\lambda 1, \lambda 2$ and k' represents the ratio of absorbance of the specific component at the two isosbestic point wavelengths $\lambda 1, \lambda 2$.

A reference liquid storage container for storing a reference liquid used to correct the spectrum baseline may be further provided before or after the detector.

According the elution test method of the invention, it is possible to measure the degree of elution of a specific component by way of the ultraviolet absorption method even when the specific component tends to change or in case impurities are contained. This conducts an elution test with a short analysis time.

Use of a differential value to obtain two isosbestic point wavelengths instead of an absorption spectrum can eliminate the influence of an impurity component.

According the elution test apparatus of the invention, it is possible to conduct an elution test of a preparation to be measured, by way of the absorbance measurement method, even when the specific component tends to change or in case impurities are contained. This conducts an elution test with a short analysis time.

Again, further providing a reference liquid storage container for storing a reference liquid used to correct the spectrum baseline to an elution tester can correct the spectrum. This provides apparatus that calculates the degree of elution more precisely.

DETAILED DESCRIPTION OF THE INVENTION

Embodiments of the invention are described below.

Figure 1:
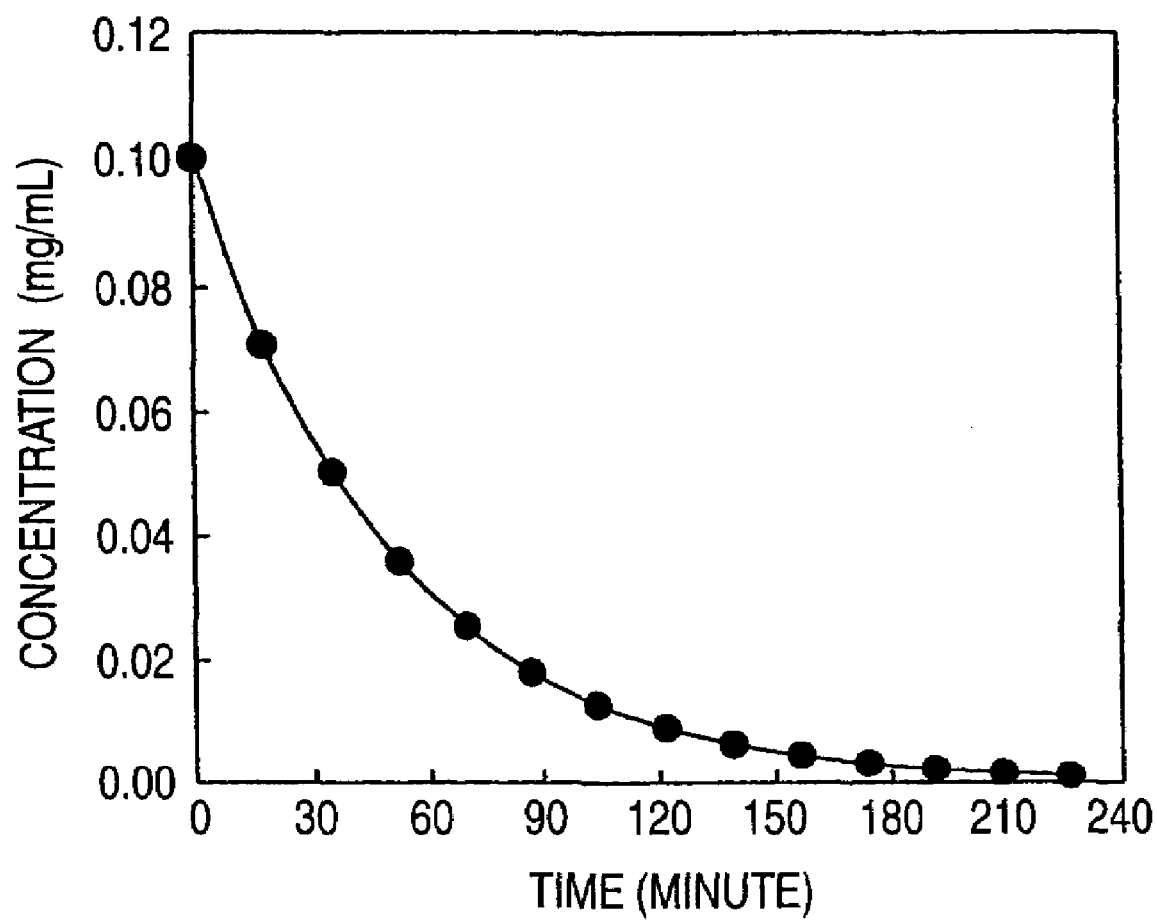
FIG. 1 shows a change with time of the residual concentration of a specific component A after the specific component A is eluted into a test liquid.

FIG. 1 shows a change with time of the residual concentration of a specific component A after the specific component A is eluted into a test liquid. The specific component A is an unstable pharmaceutical in an elution test under neutral condition and is sodium rabepranazole. The test liquid used to the elution test is a 50 mM phosphoric acid buffer solution (pH6.8, 37° C.) in order to neutralize the elution condition for the specific component A.

The residual concentration of the specific component A in the solution has been obtained by eluting the specific component A to provide the specific component A of 0.1 mg/mL in the 50 mL phosphoric acid buffer solution, performing HPLC analysis every 15 to 20 minutes and obtaining the peak area value of the specific component A, and calculating the residual concentration by using as a control the peak area value of a standard liquid being a solution of the specific component A where the specific component A does not change.

The residual concentration of the specific component A is determined to decrease, within 40 minutes, to 0.05 mg/mL, which is half the initial concentration. This verifies that the specific component A changes in the test liquid.

Figure 2:
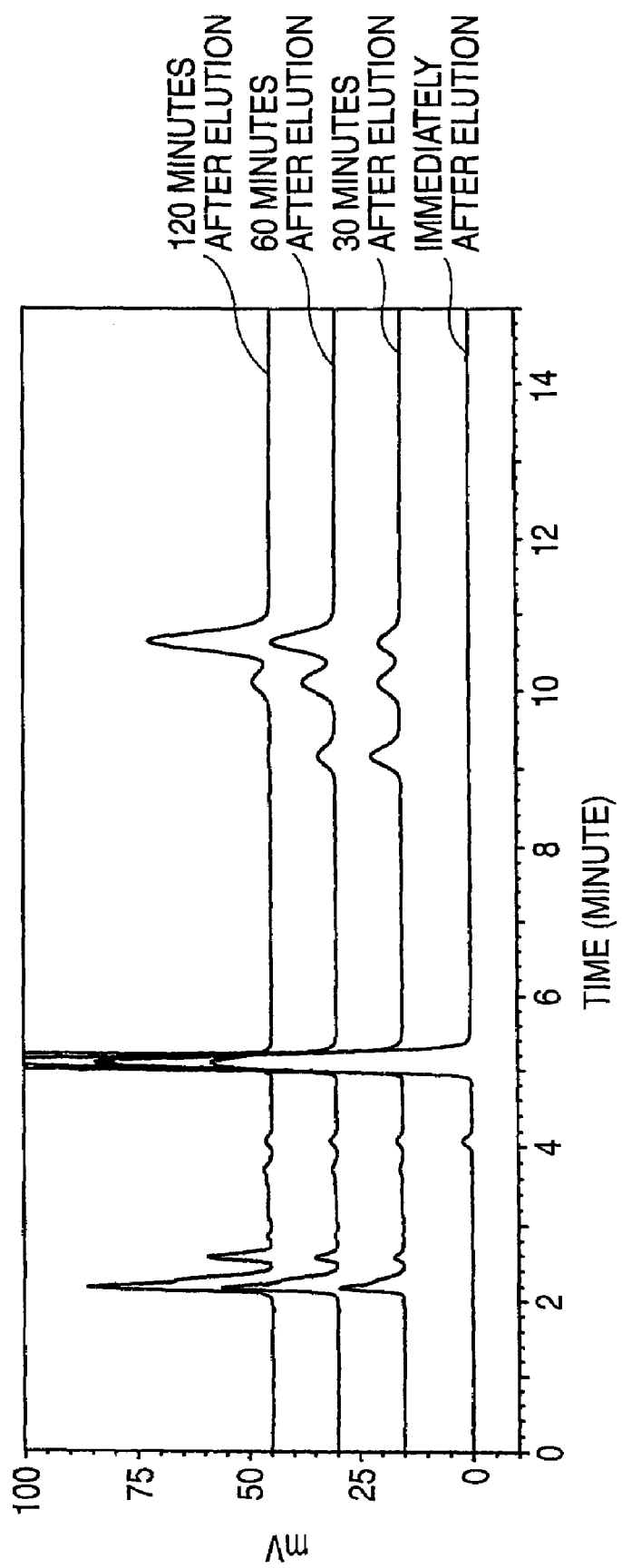
FIG. 2 shows a liquid chromatogram assumed after elution of the specific component A into the test liquid.

FIG. 2 shows a liquid chromatogram immediately after elution, 30 minutes after elution, 60 minutes after elution, and 120 minutes after elution following elution of the specific component A into the 50 mM phosphoric acid buffer solution (pH6.8, 37° C.). This figure shows a transition assumed when the specific component A changes to the decomposed matter A'.

A large peak around 5 minutes of holding time corresponds to the specific component while the peaks to the right or left of the peak correspond to the impurity component A'. The specific component A changes with time to the decomposed matter A' in the test liquid so that it is understood that it is difficult to determine the specific component A alone by the related-art absorbance measurement method without selectivity.

Figure 3:
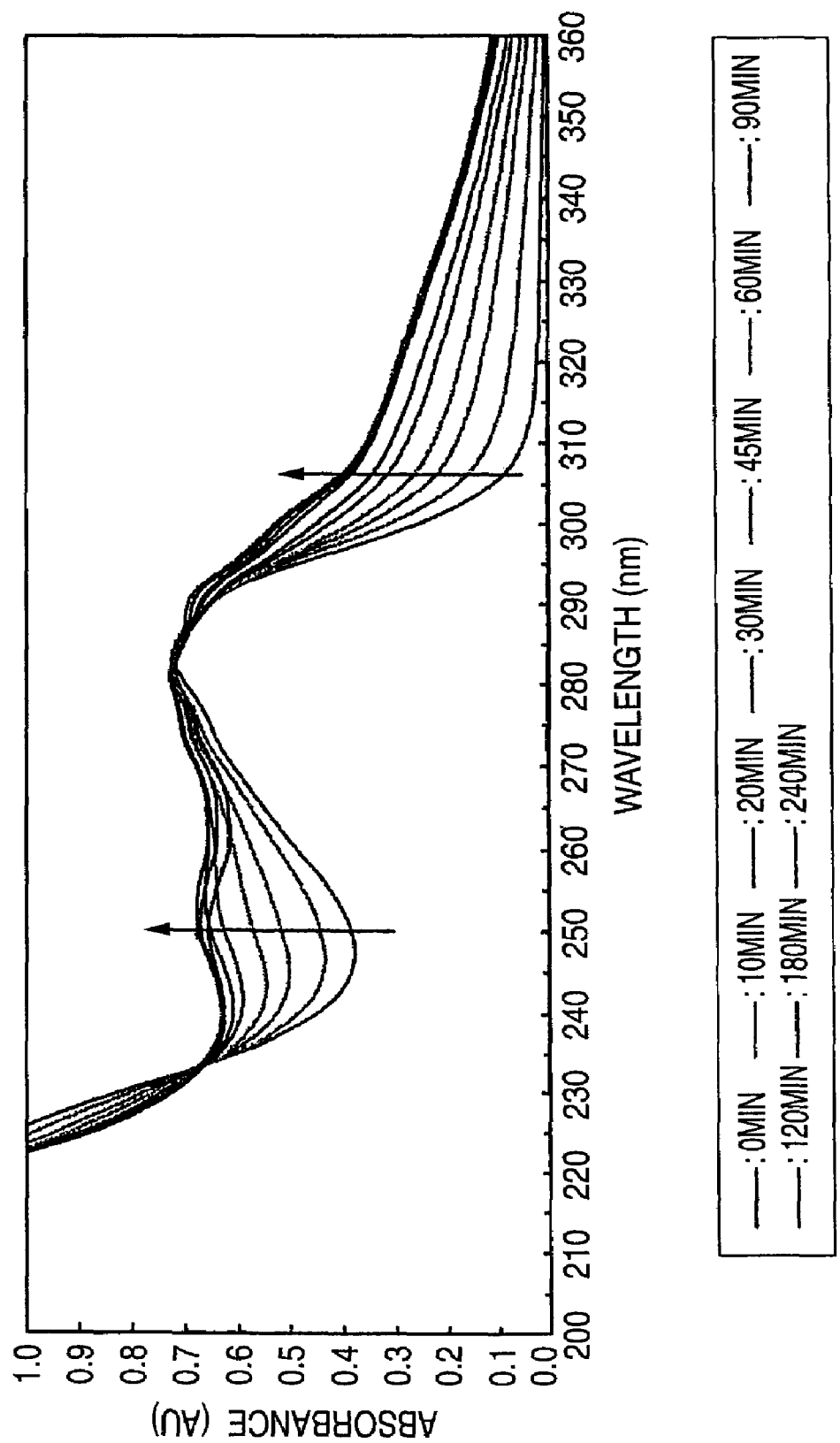
FIG. 3 shows the change with time of the specific component A in the absorption spectrum of 200 nm to 360 nm; the isosbestic point wavelengths are determined to be 234 nm and 287 nm.

FIG. 3 shows the change with time of the specific component A in the ultraviolet absorption spectrum of 200 nm to 360 nm. As the specific component A, sodium rabepranazole of 0.02 mg/mL was used. As the test liquid, 50 mM phosphoric acid buffer solution (pH6.8, 37° C.) was used.

The specific component A tends to change under these conditions so that the absorption spectrum changed with time as shown in the figure. Absorbance at the wavelengths of 234 nm and 287 nm experiences a negligible change and presence of an isosbestic point was determined.

In case a specific component easily change in a test liquid, it is possible to make measurement while selecting as an isosbestic point wavelength a wavelength where the absorbance of a system including the specific component A and its decomposed matter A' does not a change with time. The preparation C containing the specific component A also contains an impurity component B for the specific component A, for example hypro-mellosephtalate of 0.01 mg/mL. The impurity component B may be ascorbic acid or raben as well.

Figure 4:
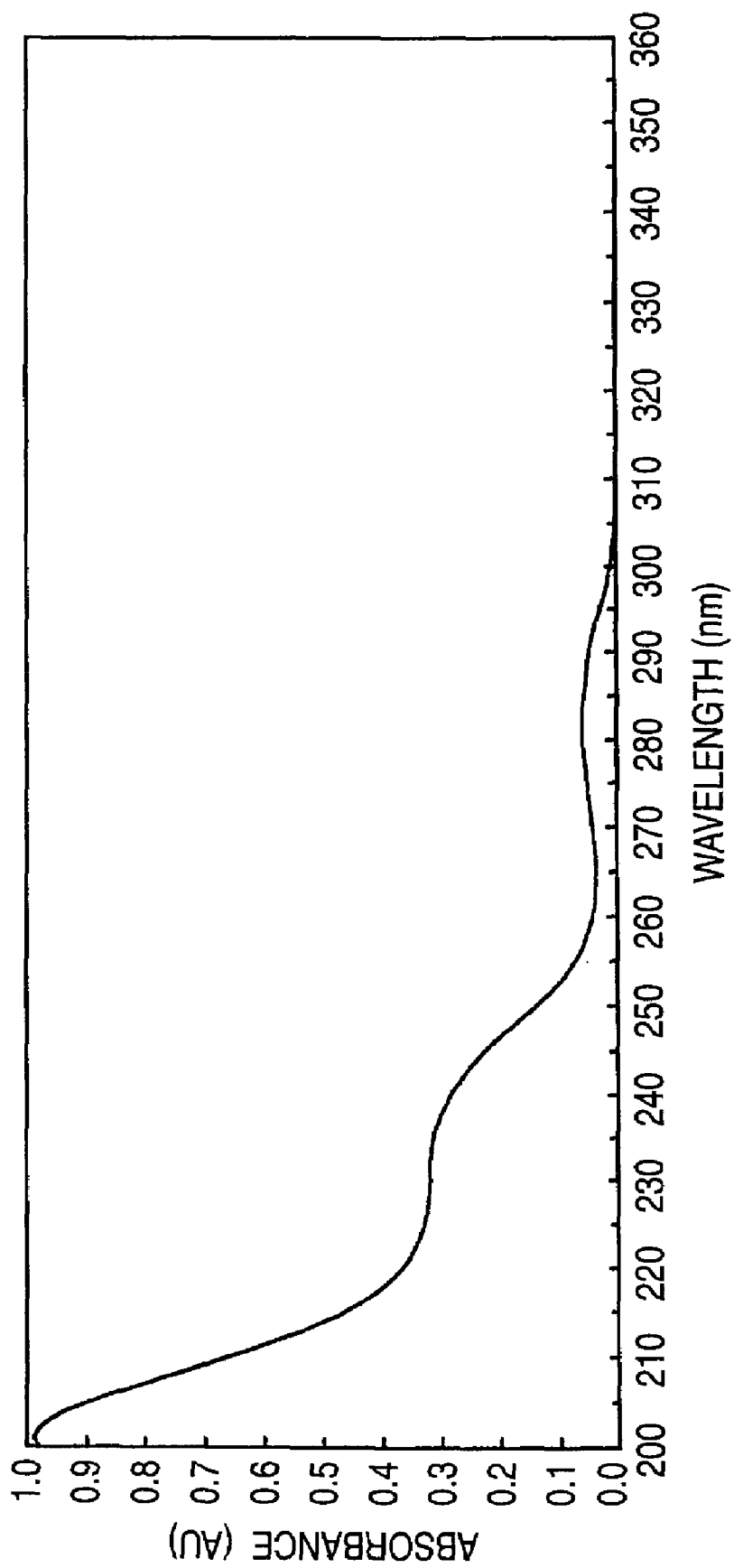
FIG. 4 shows the absorption spectrum of an impurity component B.

FIG. 4 shows the ultraviolet absorption spectrum of hypro-mellosephtalate as an impurity component B in the wavelength of 200 nm to 360 nm. The absorbance of the impurity component B is constant without changing with time and has absorption in the ultraviolet area below 300 nm.

Figure 5:
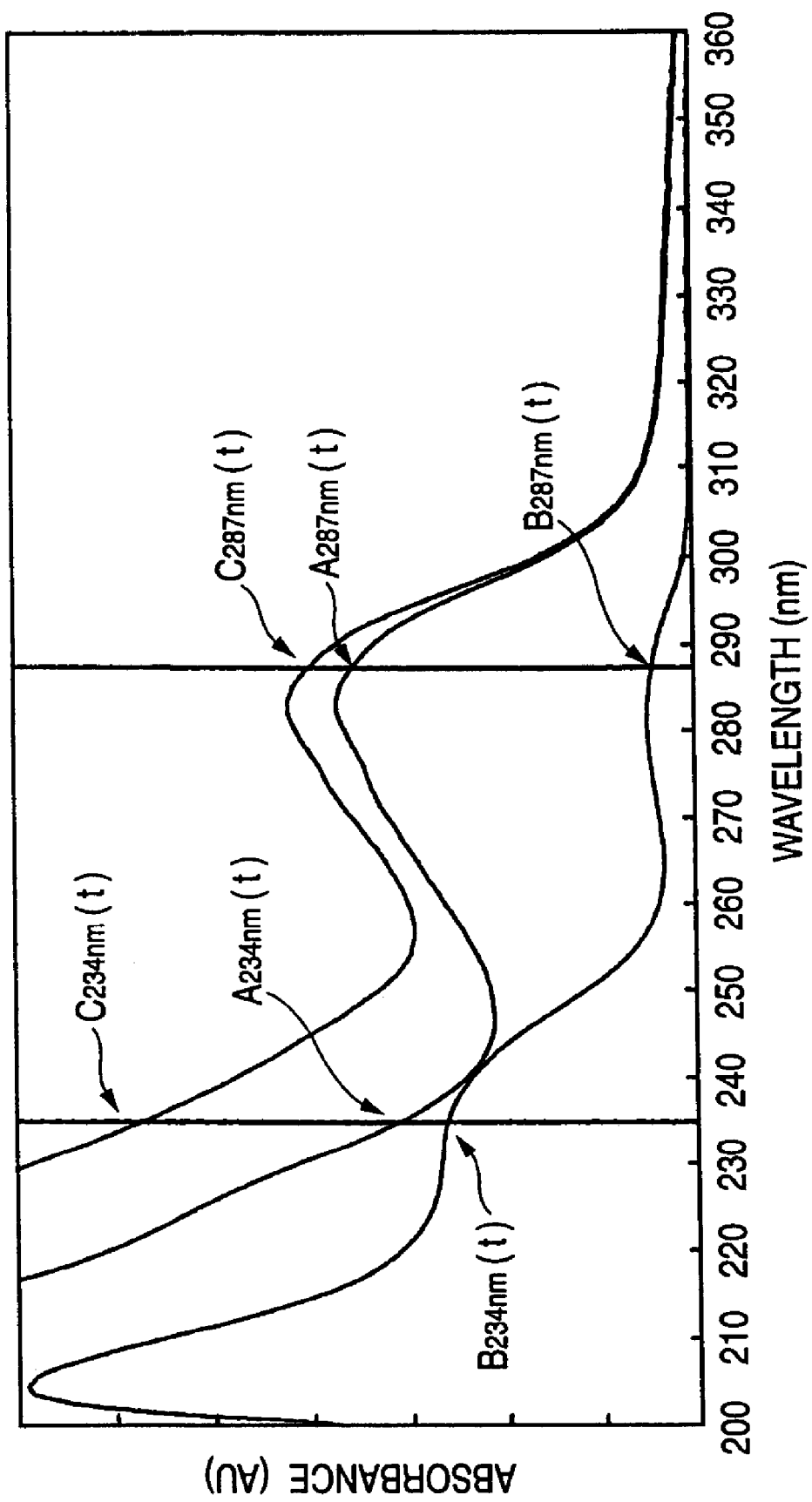
FIG. 5 shows an absorption spectrum in a system including the specific component A alone, the impurity component B alone or a mixture of the components A and B.

FIG. 5 shows an absorption spectrum at a time t in the wavelength of 200 nm to 360 nm assumed when the specific component A alone, impurity component B alone or a mixture of the components A and B is contained in a test liquid.

The following describes a method for determining the specific component A alone while eliminating the influence of the impurity component B that hinders determination from the test liquid into which the specific component A and the impurity component B are eluted from the preparation C The wavelengths to be set are 234 nm ($\lambda 1$) and 287 nm ($\lambda 2$) as isosbestic point wavelengths in a system including the specific component A and its decomposed matter in the preparation C. Assuming that the absorbances of the specific component A as $A_{234nm}(t)$ and $A_{287nm}(t)$ and the absorbances of the impurity component B as $B_{234nm}(t)$ and $B_{287nm}(t)$, the absorbances of the synthesis spectrum $C_{234nm}(t)$ and $C_{287nm}(t)$ will be represented as follows.

$$C_{234nm}(t) = A_{234nm}(t) + B_{234nm}(t) \tag{3}$$

$$C_{287nm}(t) = A_{287nm}(t) + B_{287nm}(t) \tag{4}$$

Considering the spectrum of the impurity component B, the ratio of absorbance of the wavelengths of 234 nm and 287 nm is constant and independent of time (or concentration). This obtains the expression (5).

$$B_{234nm}(t)/B_{287nm}(t) = k \tag{5}$$

where k is an absorbance ratio of 234 nm to 287 nm of the impurity component. This value is independent of time and constant so that it is an absorbance ratio that may be previously calculated as a constant.

When the expressions (3) and (4) are substituted into the expression (5), the following expression is obtained:

$$\{C_{234nm}(t) - A_{234nm}(t)\}/\{C_{287nm}(t) - A_{287nm}(t)\} = k \tag{6}$$

Expanding the expression (6) obtains the expression (7).

$$k \times C_{287nm}(t) - C_{234nm}(t) = k \times A_{287nm}(t) - A_{234nm}(t) \tag{7}$$

The ratio of $A_{234nm}(t)$ to $A_{287nm}(t)$ is constant without a change with time so that $$A_{234nm}(t)/A_{287nm}(t) = k' \tag{8}$$

The expression (7) indicates that the volume of the specific component A may be determined under the condition of a solution containing an impurity component and the specific component A, given the absorbance measurement value at 234 nm and 287 nm of the absorption spectrum of the elution test liquid and the constant k.

k and k' are constants. From the absorbance measurement values at two isosbestic point wavelengths of the elution test liquid, the concentration of the specific component A alone is obtained by solving the simultaneous equation of the expression (7) and (8).

Figure 6:
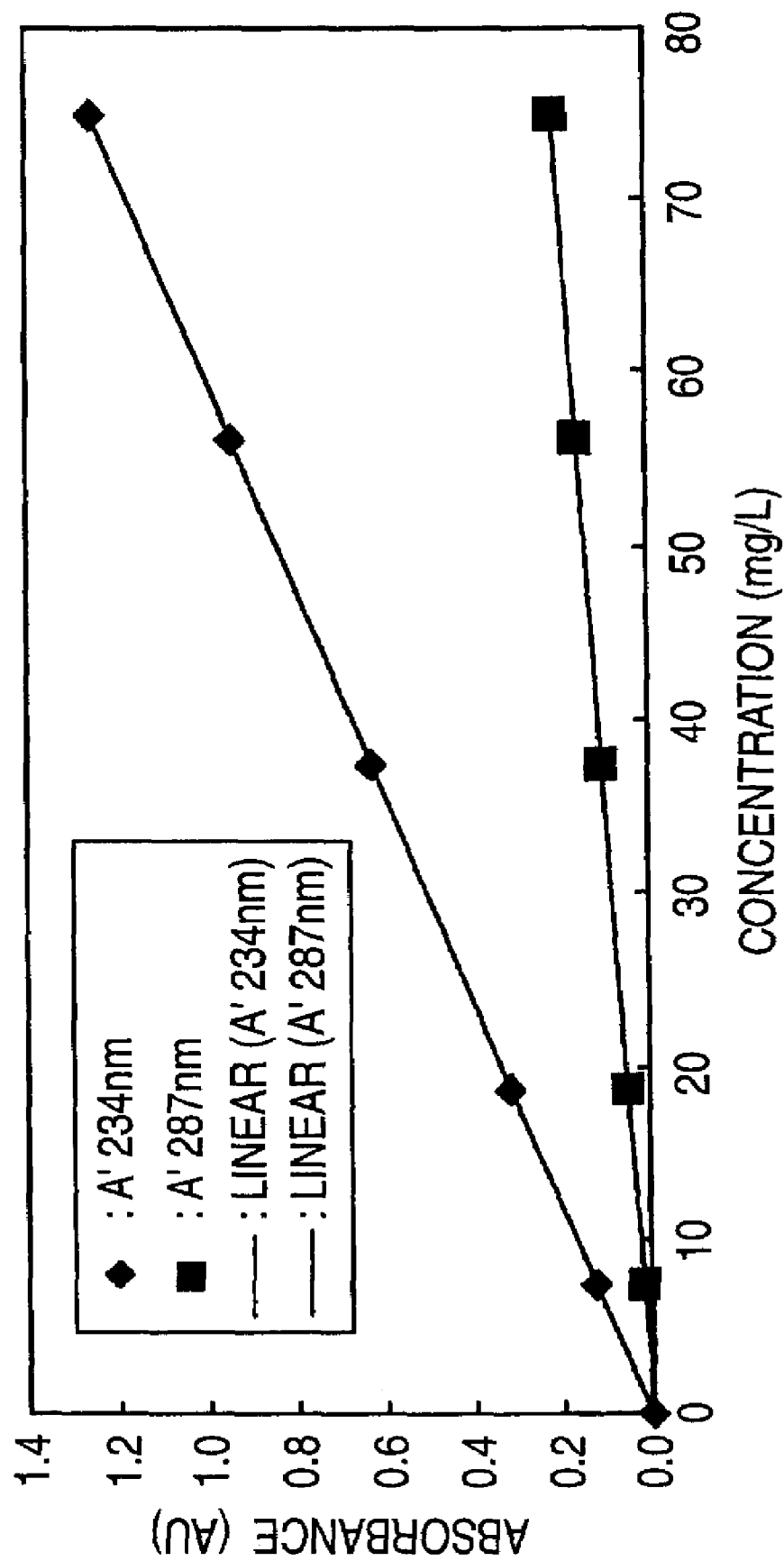
FIG. 6 shows an example of calculation of the ratio of absorbance k.

An example illustrating the expression (5) will be described referring to FIG. 6. The vertical axis represents absorbance and the horizontal axis the concentration of the impurity component B.

Solutions containing impurity components B of various concentrations (0-700 mg/mL) are prepared. From the inclination of a straight line of absorbances at two wavelengths (234 nm, 287 nm) plotted with respect to the concentration, the ratio of concentration is calculated to obtain k=5.9.

Figure 7:
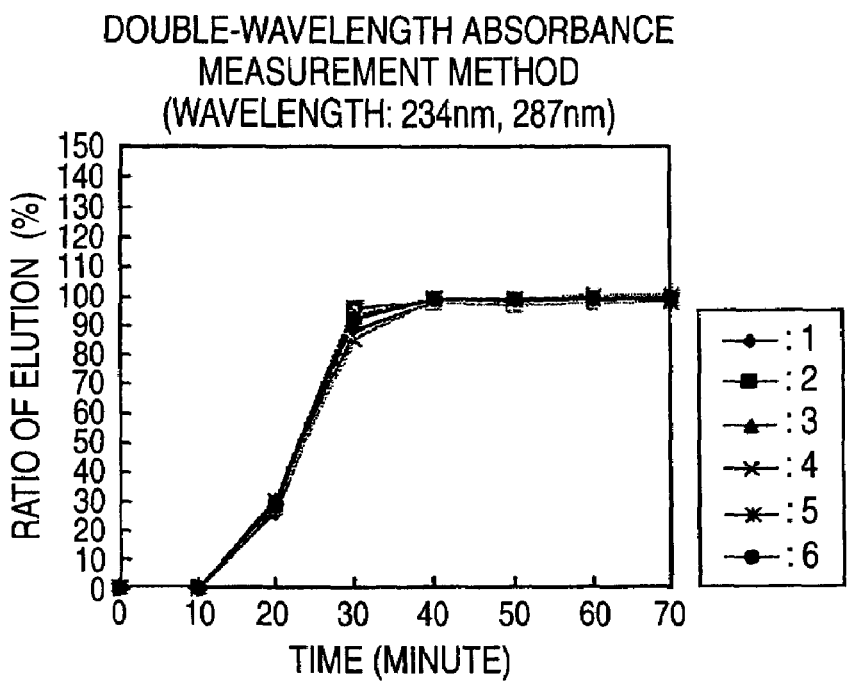
FIG. 7 shows the result of calculation of the elution concentration of the specific component A by using the single-wavelength absorbance measurement method or the double-wavelength absorbance measurement method.
Figure 7:
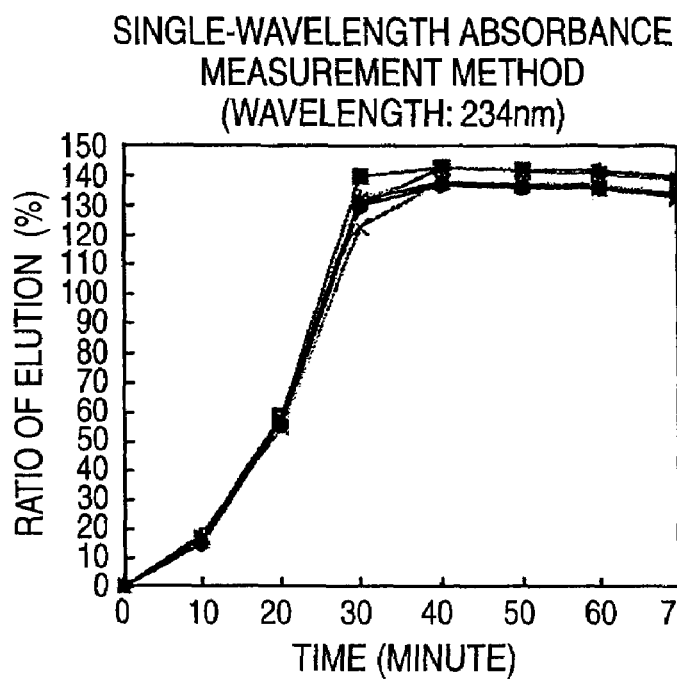

FIG. 7 shows the result of the single-wavelength absorbance measurement method (right in the figure) measuring the elution concentration of the specific component A with one wavelength and the result of the inventive double-wavelength absorbance measurement method (left in the figure) measuring the elution concentration of the specific component A with two wavelengths. The elution test method specifies that testing is made on six specimens and the elution ratios obtained from individual specimens fall within the value range stipulated in the articles concerning pharmaceuticals, the specimens are determined conforming. Thus, testing was made on six specimens. Six measurement results of these specimens by way of the inventive method show a good match.

The result of the single-wavelength absorbance measurement method (234 nm) was an elution ratio of 140 percent while the result of the double-wavelength absorbance measurement method (234 nm and 287 nm) was around 100 percent, which makes sure that the influence of an impurity component is eliminated.

While the inventive double-wavelength absorbance measurement method uses the expressions (3) through (8), the single-wavelength absorbance measurement method is specified in the Japanese Pharmacopoeia. For example, the cephalexin slow-release grain method measures the absorbances $A_T$ and $A_S$ at the wavelength of 262 nm for an eluate of a specimen solution and an eluate of a standard solution by using a collapse test liquid as a control liquid, and calculates the target elution ratio from the expression (9).

$$\text{Elution ratio (\%)} = W_S \times (A_T \text{ and } A_S) \times (V'/V) \times (1-C) \times 90 \quad (9)$$

where $W_S$ is a volume (mg (potency)) of a cephalexin standard solution, for example. Visa filtrate volume V mL without the initial filtrate (for example 10 mL). V' is a specimen solution volume V' mL after a collapse test so as to include for example cephalexin in the filtrate volume V mL. C is the indicated volume (mg (potency)) of cephalexin in a package.

Figure 8:
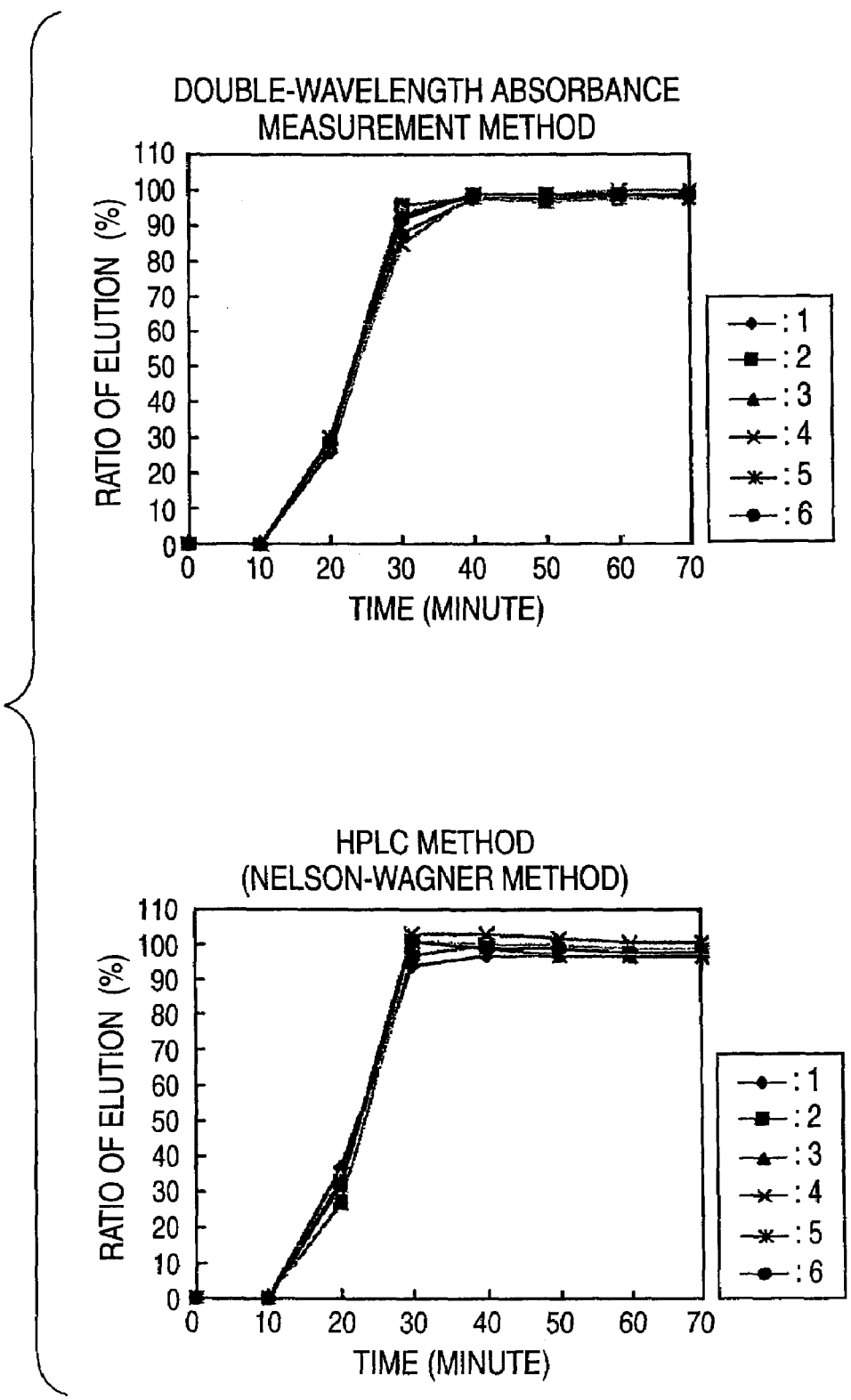
FIG. 8 compares the result of calculation of the elution concentration of the specific component A by using the inventive double-wavelength absorbance measurement method with the result of the same by using the HPLC method with correction by way of the Nelson-Wagner method.

FIG. 8 compares the result of the inventive double-wavelength absorbance measurement method (left in the figure) with the result of the HPLC method (right in the figure) that is based on the Nelson-Wagner method. In this example also, testing is made by using six specimens.

It is determined that the inventive double-wavelength absorbance measurement method obtains substantially the same result as the result of the HPLC method (after Nelson-Wagner correction).

Figure 9:
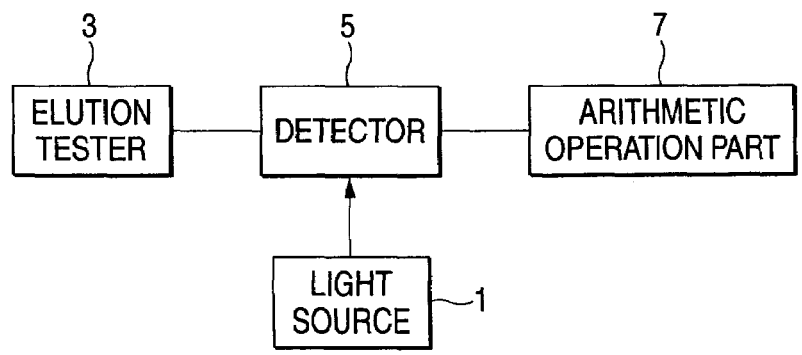
FIG. 9 shows an embodiment of the elution test apparatus according to the invention.
Figure 10:
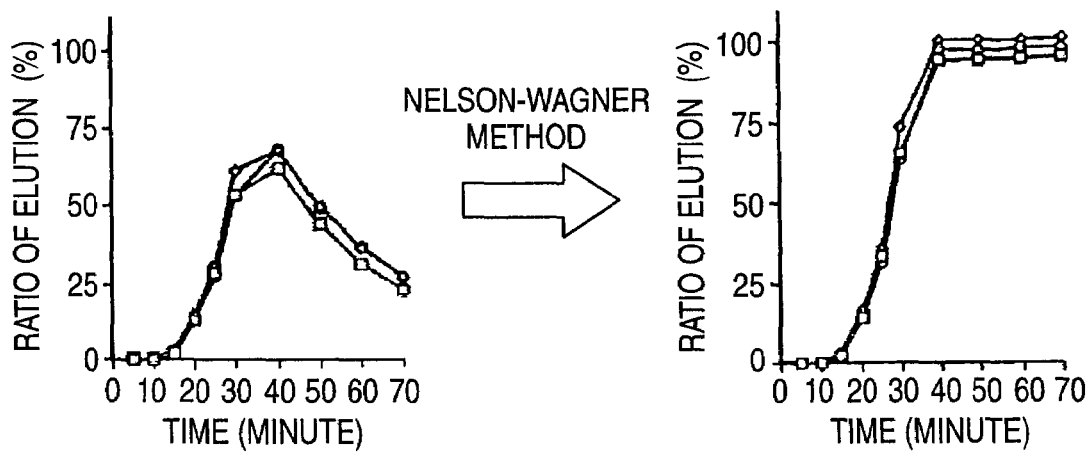
FIG. 10 us an elution profile calculated by way of the Nelson-Wagner method.

FIG. 9 is a block diagram of elution test apparatus according to the invention.

The elution test apparatus according to the invention comprises an elution tester 3 for eluting the preparation to be measured into an elution test liquid, a detector 5 and an arithmetic operation part 7.

The detector 5 comprises a flow cell. The detector 5 also comprises a passage for collecting the elution test liquid in the elution tester 3 periodically or at an arbitrary point and sending the liquid into the flow cell and returning the liquid from the flow cell to the elution tester 3. In the detector 5, a light source 1 irradiates light onto the elution test liquid in the flow cell to measure the absorbance at two wavelengths $\lambda 1$, $\lambda 2$. The two wavelength $\lambda 1$, $\lambda 2$ are two isosbestic point wavelengths of in a system including the specific component and its decomposed matter contained in the preparation to be measured.

The arithmetic operation part 7 calculates at least one of the absorbances A1(t), A2(t) of the specific component by using $$k \times C2(t) - C1(t) = k \times A2(t) - A1(t) \text{ and}$$

$$A1(t)/A2(t) = k'$$

from the absorbance C1(t), C2(t) at the two isosbestic point wavelengths $\lambda 1$, $\lambda 2$ measured at the plural time points t in the elution process of the preparation and converts the result to an elution concentration. k represents the ratio of absorbance of the impurity component at the two isosbestic point wavelengths $\lambda 1$, $\lambda 2$ and k' represents the ratio of absorbance of the specific component at the two isosbestic point wavelengths $\lambda 1$, $\lambda 2$.

The elution tester 3 may be any one that is well known.

A reference liquid storage container for storing a reference liquid used to correct the spectrum baseline may be further provided to the elution tester 3.

The invention provides apparatus for calculating the degree of elution of a specific component with the influence of an impurity component removed. Further, providing a reference liquid storage container for storing a reference liquid can correct the spectrum. This provides apparatus that calculates the degree of elution more precisely.

The invention is not limited to the foregoing embodiments but may be executed within the scope defined by the claims. For example, an isosbestic point wavelength may be determined by selecting a wavelength where the absorption strength of the differential spectrum of a specific component is not subject to a change with time. In this case, the first-order differential value, the second-order differential value, the third-order differential value, or a higher-order differential value of the spectrum may be used. In case more than two isosbestic point wavelengths are obtained, the invention may be implemented based on two isosbestic point wavelengths selected therefrom.

The invention is applicable to an elution test of any pharmaceutical preparation available on the market including a compound having absorption in the ultraviolet area or visible area.

We claim:

1. A method for measuring an elution process of a specific component in a process where a preparation containing at least the specific component subject to a change with time in chemical properties after elution and an impurity component not subject to a change with time in chemical properties after elution is eluted into a test liquid, said method comprising:

obtaining a ratio of absorbance k of said impurity component and a ratio of absorbance k' of said specific component at two isosbestic point wavelengths $\lambda 1$, $\lambda 2$ in a system including said specific component and its decomposed matter;

measuring at each time the absorbance C1(t), C2(t) in said two isosbestic point wavelengths for said test liquid at plural time points t of the elution process of said preparation and calculating at least one of the absorbances A1(t), A2(t) of said specific component by using the relations: $k \times C2(t)-C1(t)=k \times A2(t)-A1(t)$ and $A1(t)/A2(t)=k'$; and converting the result to an elution concentration.

2. The elution test method according to claim 1, wherein said two isosbestic point wavelengths have been obtained based on a differential value of absorbance.

3. The elution test method according to claim 2, wherein said differential value is a first-order differential value, a second-order differential value, or a third-order differential value.

4. An elution test apparatus comprising:

an elution tester for eluting a preparation to be measured into a test liquid;

a detector for irradiating light onto an eluate from the elution tester and measuring an absorbance at two isosbestic point wavelengths $\lambda 1$, $\lambda 2$ in a system including a specific component and its decomposed matter contained in the preparation to be measured; and an arithmetic operation part for calculating at least one of the absorbances A1(t), A2(t) of said specific component by using $$k \times C2(t)-C1(t)=k \times A2(t)-A1(t) \text{ and}$$

$$A1(t)/A2(t)=k'$$

from the absorbance C1(t), C2(t) at said two isosbestic point wavelengths $\lambda 1$, $\lambda 2$ measured at the plural time points t in the elution process of said preparation, and converting the result to an elution concentration, wherein k represents the ratio of absorbance of said impurity component at said two isosbestic point wavelengths $\lambda 1$, $\lambda 2$ and k' represents the ratio of absorbance of said specific component at said two isosbestic point wavelengths $\lambda 1$, $\lambda 2$.

5. The elution test apparatus according to claim 4, further comprising:

a reference liquid storage container for storing a reference liquid used to correct the spectrum baseline.

* * * * *